US007748901B2

(12) United States Patent
Markoff et al.

(10) Patent No.: US 7,748,901 B2
(45) Date of Patent: Jul. 6, 2010

(54) UNIVERSAL X-RAY TEST BED

(75) Inventors: Nickolas Markoff, Golden, CO (US); Christopher M. Cone, Golden, CO (US); Mike M. Tesic, Louisville, CO (US)

(73) Assignee: Unisyn Medical Technologies, Inc., Golden, CO (US)

( * ) Notice: Subject to any disclaimer, the term of this patent is extended or adjusted under 35 U.S.C. 154(b) by 196 days.

(21) Appl. No.: 12/062,894

(22) Filed: Apr. 4, 2008

(65) Prior Publication Data

US 2009/0067581 A1    Mar. 12, 2009

Related U.S. Application Data

(60) Provisional application No. 60/910,555, filed on Apr. 6, 2007.

(51) Int. Cl.
*G01D 18/00* (2006.01)

(52) U.S. Cl. .................................................. 378/207

(58) Field of Classification Search ................... 378/19, 378/58, 98.8, 117, 118, 198, 207, 189; 250/252.1, 250/370.09; 324/501
See application file for complete search history.

(56) References Cited

U.S. PATENT DOCUMENTS 5,473,663 A * 12/1995 Hsieh ......................... 378/207
6,212,256 B1 * 4/2001 Miesbauer et al. ........... 378/118
6,325,540 B1 * 12/2001 Lounsberry et al. .......... 378/207
6,412,980 B1 * 7/2002 Lounsberry et al. .......... 378/207
6,488,409 B1 * 12/2002 Vafi et al. .................... 378/207
6,663,281 B2 * 12/2003 Aufrichtig et al. ........... 378/207
6,693,668 B1 * 2/2004 May et al. .................... 348/247
6,777,949 B2 * 8/2004 Tsuji et al. ................... 324/501
6,872,949 B2 * 3/2005 Mizuoka et al. ............. 250/358.1
6,883,963 B2 * 4/2005 Nolewaika ................... 378/207
6,919,568 B2 * 7/2005 Odogba et al. ............. 250/370.09

* cited by examiner

*Primary Examiner*—Allen C. Ho
(74) *Attorney, Agent, or Firm*—Stoel Rives LLP (57) ABSTRACT

Systems and methods presented herein provide for the testing and reconfiguration of x-ray devices. In one embodiment, a test bed effectuates testing of an acquired x-ray device to determine a cause of the inoperability of the device. The x-ray device test bed may be provided to test a plurality of x-ray devices and, therefore, readily adaptable to such devices. The x-ray device test bed may include a mount for an x-ray tube. A variable power supply may be coupled to the x-ray tube to provide the requisite high-voltage electrical energy thereto. The x-ray device test bed may also include a mount for an imaging module (e.g., a "flat-panel sensor"). A processor may be coupled to the imaging module to determine the operational characteristics thereof. If certain x-ray components are deemed inoperable, the x-ray components may be replaced such that the x-ray device may be reintroduced to a medical industry segment.

24 Claims, 6 Drawing Sheets

UNIVERSAL X-RAY TEST BED

CROSS REFERENCE TO RELATED APPLICATIONS

This patent application claims priority to and thus the benefit of an earlier filing date from U.S. Provisional Patent Application No. 60/910,555 (filed Apr. 6, 2007), the entire contents of which are hereby incorporated by reference.

BACKGROUND

Generally, manufacturers of medical equipment, such as General Electric, Siemens, Phillips, build and service the medical equipment that they develop. These manufacturers maintain detailed specifications and circuit diagrams for the equipment such that their service technicians can perform repairs and they vigilantly protect that information in order to protect their market share. For example, by closely guarding the specifications and diagrams of the x-ray device, the manufacturer may prevent others from entering the market to service and repair their brand-name devices. And, by monopolizing the service and repair market for a particular piece of equipment, the manufacturer is able to extrude even more income from a sale thereof. Accordingly, the service and repair costs associated with that device can be quite substantial, even while the sale price of a particular x-ray device is also very substantial.

In many cases, medical devices are almost prohibitively expensive. For example, doctors and hospitals in smaller markets (e.g., small towns) are often unable to afford the costs associated with such devices. Even if it were possible for the smaller market medical service providers to afford these medical devices, the costs associated with the service and repair of the devices would likely put the devices' benefits out of economic reach.

SUMMARY

Systems and methods presented herein (hereinafter referred to as the "utility") provide for the testing, servicing, and reintroduction of electronics into an industry segment. More specifically, medical equipment, such as x-ray devices are acquired and configured for reintroduction into an operable status. In one embodiment, the utility provides for the identification and acquisition of a medical device from a medical industry segment. For example, the utility may provide a means for acquiring certain medical equipment such that they may be tested and/or serviced and subsequently reintroduced into an operational status for use in a medical industry segment, such as a hospital or a doctor's office.

In one embodiment, the medical equipment is acquired in a malfunctioning or at least a partially inoperable status. For example, a hospital, a doctor's office, medical device manufacturer, or the like, may possess an x-ray device, or other radiation type medical device, that is not operational. The utility may receive information pertaining to the medical device that indicates the type of medical device and the original manufacturer. An acquisition module may receive the medical device, for example, by purchasing the medical device from the medical industry segment. Such a purchase may effectively transfer title of the medical device to the acquisition module. In this regard, the cost of such an acquisition may be substantially less than the original sale price of the medical device due, at least in part, to the inoperable nature of the medical device.

After the medical device has been acquired, a test module (e.g., a test bed) may effectuate testing of the acquired device to determine a cause of the inoperability of the medical device. In this regard, the test module may be readily adaptable to a plurality of medical devices. For example, an x-ray device test bed may be provided to test a plurality of x-ray devices. Such x-ray devices may be from the same or different manufacturers. The x-ray device test bed may include a mount that receives and supports an x-ray tube of the x-ray device under test. A variable power supply may be coupled to the x-ray tube to provide the requisite high-voltage electrical energy thereto. The x-ray device test bed may also include another mount that receives and supports an imaging module (e.g., a "flat-panel sensor" that includes a charge coupled device, or "CCD") of the x-ray device under test. A processor may be configured with the test bed and coupled to the imaging module of the x-ray device to determine the operational characteristics of the imaging module and the x-ray tube. For example, the processor may determine certain pixels of the imaging module that are not functioning. In this regard, the processor may ascertain whether a certain level of resolution may still be obtained with the imaging module (e.g., an acceptable percentage of pixels that are still operable). If certain x-ray components are deemed to be inadequate in terms of operational functionality, the x-ray components may be replaced such that the x-ray device may be reintroduced to a medical industry segment.

In one embodiment, a universal x-ray test bed is provided that allows for the service and repair of virtually any x-ray device on the market. The test bed includes a housing with x-ray components being mountable in a vertical fashion therein. For example, the housing may include an x-ray tube mount used to readily adapt to x-ray tubes of a variety of x-ray device manufacturers. The housing also includes a imaging module mount that is adaptable to retain an imaging module of a corresponding x-ray tube manufacturer. The housing is also configured with an adaptable power supply that readily adjusts to the power requirements of a mounted x-ray tube and/or the imaging module. Additionally, the housing includes a communication interface that couples with the imaging module mount to transfer information from the imaging module to a diagnostic module. The diagnostic module (e.g., a computer work station) may, in turn, use this information and determine, e.g., whether imaging module pixels are still functional and/or determine the existing capability of the imaging module. The diagnostic module may also provide a report describing the existing capabilities of the x-ray components such that a subsequent purchaser may make an informed purchase of a reconditioned x-ray device. In one embodiment, the diagnostic module provides a pixel map illustrating which pixels of the imaging module are no longer operational.

The utility may also provide a means for warranting the x-ray device in a medical industry segment. In one embodiment, the means for warranting includes warranting a reintroduced x-ray device. For example, when an x-ray device has been tested and brought into condition for reintroduction into the medical industry segment, the means for warranting may provide a level of reassurance in case the reintroduced x-ray device fails. Such warranting may include repair service and/or replacement service. In another embodiment, the means for warranting may include warranting an originally introduced x-ray device of an original equipment manufacturer. For example, when an original equipment manufacturer initially introduces an x-ray device to a medical industry segment, the manufacturer often provides a warranty that covers the cost of repairs and/or replacements. However, this warranty coverage is generally for a limited period of time. Once the warranty period ends, the utility may provide for warranting the medical device for a period of time thereafter. In this regard, utility may provide for assessing the x-ray device while in the medical industry segment to determine an appropriate amount of warranty coverage. While under coverage, the utility may provide repairs and/or replacements in a manner similar to an original equipment manufacturer warranty.

In one embodiment, a test bed for use with a plurality of x-ray device types includes a housing that includes a first support member and a second support member, wherein the first support member is configured for retaining an x-ray tube and wherein the second support member is configured for retaining an imaging module of the plurality of x-ray device types. The test bed also includes a high-voltage power supply configured for selectively providing a plurality of voltage levels and for being adapted to provide at least one of the voltage levels to the x-ray tube and a processor communicatively coupled to the imaging module to retrieve electronic data from the imaging module where in the processor processes the electronic data to determine at least one inoperable component of the imaging module. The first support member may be further configured for retaining the x-ray tube of the plurality of x-ray device types. A first x-ray device of the plurality of x-ray device types may be manufactured by a first x-ray device manufacturer and a second x-ray device of the plurality of x-ray device types may be manufactured by a second x-ray device manufacturer that is different from the first x-ray device manufacturer.

The test bed may further include a storage element that stores a first software module, wherein the first software module directs the processor to generate a report that includes information associated with at least one inoperable pixel of the imaging module. The storage element further stores a second software module that controls a rules processing engine, wherein the rules processing engine is configured for receiving the information associated with the least one inoperable pixel of the imaging module to determine a requisite compliance. The requisite compliance may include a standard, a government regulation, or both.

The test bed may further include a display interface configured for displaying an image produced by operable pixels of the imaging module. The test that may further include a storage element stores a software module that directs the processor to display a location of at least one inoperable pixel with the display interface. Alternatively or additionally, the storage on may store a software module that directs the processor to locate the least one inoperable pixel of the charge coupled device. Alternatively or additionally, the software module may determine the percentage of operable pixels within the imaging module. Alternatively or additionally, the software module may determine a failure rate for the pixels of the imaging module.

In one embodiment, a method of reconfiguring a plurality of x-ray device types includes identifying a first x-ray device of a medical industry segment, wherein the first x-ray device is at least partially inoperable, acquiring the first x-ray device from the medical industry segment, and providing a test bed that adapts to a configuration of the first x-ray device. The method also includes operating the test bed to determine at least one inoperable component of the first x-ray device and replacing or repairing me the at least one inoperable component to return the first x-ray device to an operable status.

Operating the test bed may include accessing a database that stores information associated with a second x-ray device to determine the least one inoperable component of the first x-ray device, wherein the first x-ray device and the second x-ray device include a same type. The method may further include storing information, in a database, of at least a portion of the first x-ray device in response to operating the test bed. The method may also include identifying a second x-ray device of a medical industry segment, wherein the second x-ray device is at least partially inoperable, acquiring the second x-ray device from the medical industry segment, providing a test bed that adapts to a configuration of the second x-ray device, operating the test bed to determine at least one inoperable component of the second x-ray device, and replacing or repairing the at least one inoperable component to return the second x-ray device to an operable status.

The method may further include storing information, in the database, of at least a portion of the second x-ray device in response to operating the test bed for the second x-ray device. The method may further include including mapping the information of the second x-ray device to the information of the first x-ray device. Storing the information of the first and second x-ray devices may include storing the information according to manufacturer and/or type.

In one embodiment, a system for analyzing flat panel sensors of x-ray devices to determine operational characteristics of the flat panel sensors includes a radiant energy source, a high voltage source coupled to the radiant energy source stimulate emission of radiant energy from the radiant energy source, and a communication interface configured for adaptively coupling to a plurality of flat panel sensors. The system also includes a processor communicatively coupled to the communication interface to determine a type of flat panel sensor coupled to the communication interface and to process data from the flat panel sensor for use in determining one or more inoperable components of the flat panel sensor.

In one embodiment, a method of determining an operational characteristic of a flat-panel sensor of an x-ray device includes providing a test bed that includes a communication interface configured for coupling to a plurality flat-panel sensors, generating a plurality of control signals to interrogate connections between a first flat-panel sensor and the communication interface, determining, based on the interrogate connections, a type of the first flat-panel sensor, and propagating energy to the first flat-panel sensor. The method also includes extracting data from the first flat-panel sensor in response to propagating energy and processing the extracted data to determine one or more inoperable components configured with the first flat-panel sensor.

The method may further include coupling a second flat-panel sensor to the communication interface, generating a plurality of control signals to interrogate connections between the second flat-panel sensor and the communication interface, and determining, based on the interrogate connections, a type of the second flat-panel sensor. The method may also include propagating energy to the second flat-panel sensor, extracting data from the second flat-panel sensor in response to propagating energy, and processing the extracted data to determine one or more inoperable components configured with the second flat-panel sensor. The method may also include accessing a database to retrieve information about the first flat-panel sensor for comparison to information about the second flat-panel sensor. The method may also include using the comparison of the information about the first flat-panel sensor to the information about the second flat-panel sensor to determine the one or more inoperable components configured with the second flat-panel sensor. The method may further include determining a percentage of operable pixels with the first flat-panel sensor. The method may further include determining a failure rate of pixels with the first flat-panel sensor.

DETAILED DESCRIPTION OF THE DRAWINGS

While the invention is susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives falling within the scope and spirit of the invention as defined by the claims.

Figure 1:
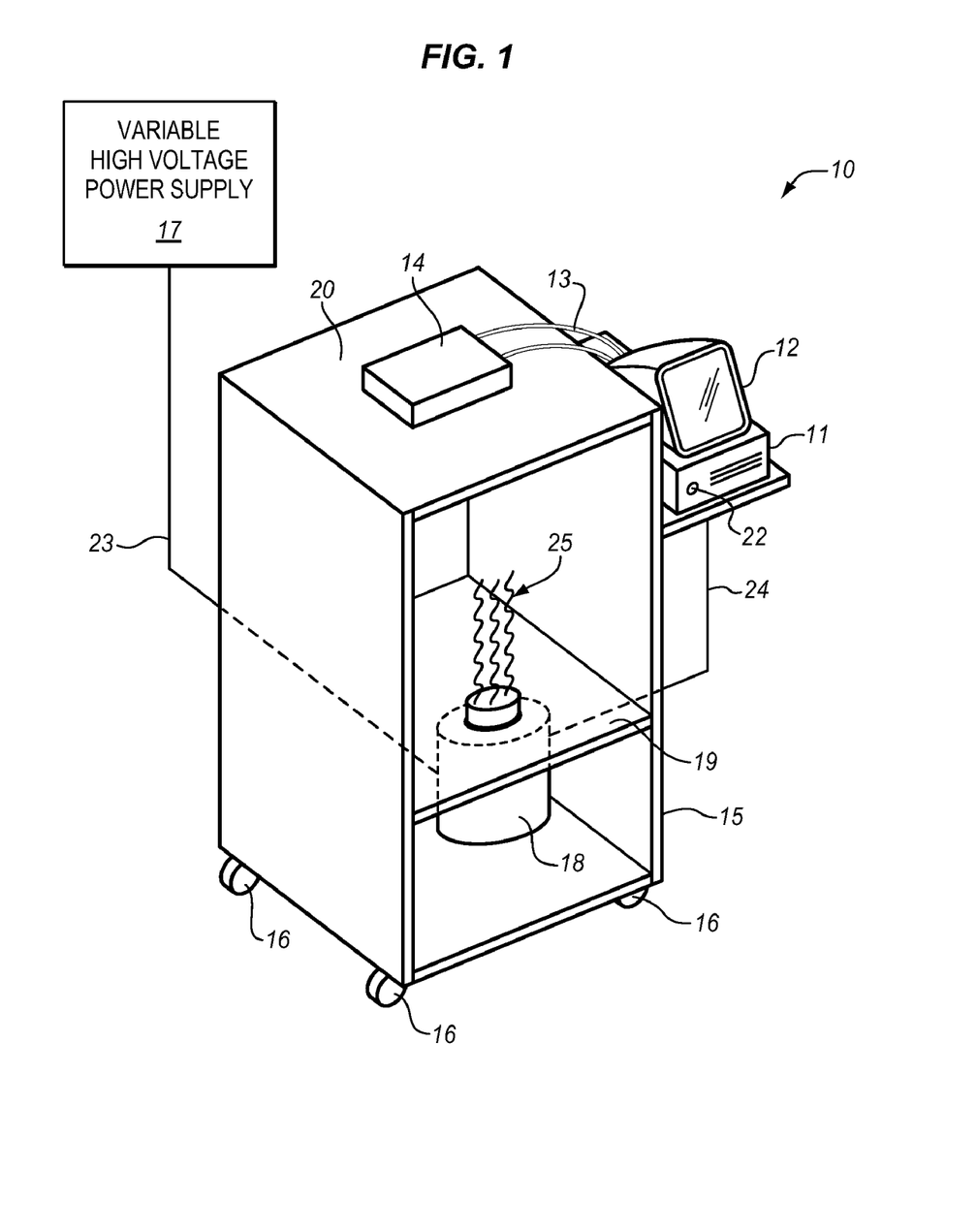
FIG. 1 is a perspective drawing of an exemplary x-ray test bed.

Turning now to the drawings, FIG. 1 is a perspective drawing of an exemplary x-ray test bed 10. The test bed 10 is generally configured as a housing 15 with mounting members 19 and 20. In this embodiment, the mounting number 19 is used to support an x-ray tube 18 whereas the mounting member 20 is used to support an imaging module 14. The imaging module 14 captures the x-rays 25 from the x-ray tube 18 and generates electronic data that is transferred to a computer workstation 11 for processing and analysis. In this regard, the computer workstation 11 may be used to identify one or more inoperable components of the imaging module 14 and/or the x-ray tube 18. The computer workstation 11 may be configured in a variety of ways that may include, for example, desktop and laptop computers.

To transfer the data from the imaging module 14 to the computer workstation 11, the test bed 10 is configured with a data link 13 that is generally configurable to transfer data from a plurality of imaging module types. In this regard, the test bed 10 may be readily configured for testing components from a plurality of x-ray devices. For example, x-ray devices are manufactured by a plurality of medical device manufacturers, such as General Electric and Siemens. These manufacturers often provide a variety of models for an x-ray device. With so many types of x-ray devices, the market for repair services is generally confined to the original equipment manufacturers of the devices. That is, each manufacturer, in general, vigilantly protects information pertaining to the design of their respective medical devices which may preclude other service organizations from repairing, refurbishing, and/or reconfiguring a variety of medical device types. The data link 13 overcomes such by providing a communication transfer from a variety of imaging module types to a test bed processor (i.e., the computer workstation 11) such that the electronic data from the imaging module 14 may be analyzed to provide a diagnosis of the imaging module 14 and/or the x-ray tube 18.

Also illustrated in this embodiment, is the variable high voltage power supply 17. The high-voltage power supply 17 is coupled to the x-ray tube 18 via the high-voltage power line 23 to provide power to the x-ray tube 18 for the generation of x-rays 25 within the housing 15. The high-voltage power supply 17, in this embodiment, is variable so as to operate with a plurality of x-ray tube types. For example, x-ray tubes come in a variety of designs with different operating voltages. To properly test a variety of x-ray tube types, the test bed 10 is generally configured with a variable high voltage power supply 17 that provides high-voltage power to an x-ray tube under test (e.g., the x-ray tube 18).

The computer workstation 11 is configured with a test activation switch 22 that controls operations the x-ray tube 18 (via connection 24) and the imaging module 14. For example, the test activation switch 22 may initiate x-ray generation from the x-ray tube 18 and correspondingly direct the imaging module 14 to capture the x-rays 25 from the x-ray tube 18. Once captured, the imaging module 14 converts the analog x-ray information of the x-rays 25 into electronic data that is processable by the workstation 11.

Generally, imaging modules, such as the imaging module 14, are configured as charge coupled devices and are commonly referred to as flat-panel sensors (although other x-ray detection means may be employed). An example of a flat panel sensor is illustrated as a block diagram in FIG. 2. The flat panel sensor 130, in this example, includes a sensor area 132 that is configured as a photodiode array. Also configured with a sensor is a shift register 131 that clocks out individual pixels from the photodiode array. For example, when an image is to be generated, the workstation 11 may initiate the test bed 10 via the test activation switch 22 and thereby initiate x-ray radiation from the x-ray tube 18. The photodiode array 132 receives photons from the x-ray radiation which are subsequently converted to analog electronic data. The shift register 131 clocks out the analog electronic data as pixels. In this regard, the sensor 130 may also include a timing pulse generator 134 to trigger the shift register 131 and an oscillator 135 to provide clock for the timing pulse generator 134. The clocked out pixels are then amplified (e.g., via the amplifier array circuits $138_{1 \ldots N}$, the buffer amplifiers $137_{1 \ldots N}$, and the processing amplifiers $138_{1 \ldots N}$). Thereafter, the analog data from the amplification is converted to digital data via the A/D converters $139_{1 \ldots N}$ and are output via the FIFO circuits $140_{1 \ldots N}$ as digital video output.

Figure 2:
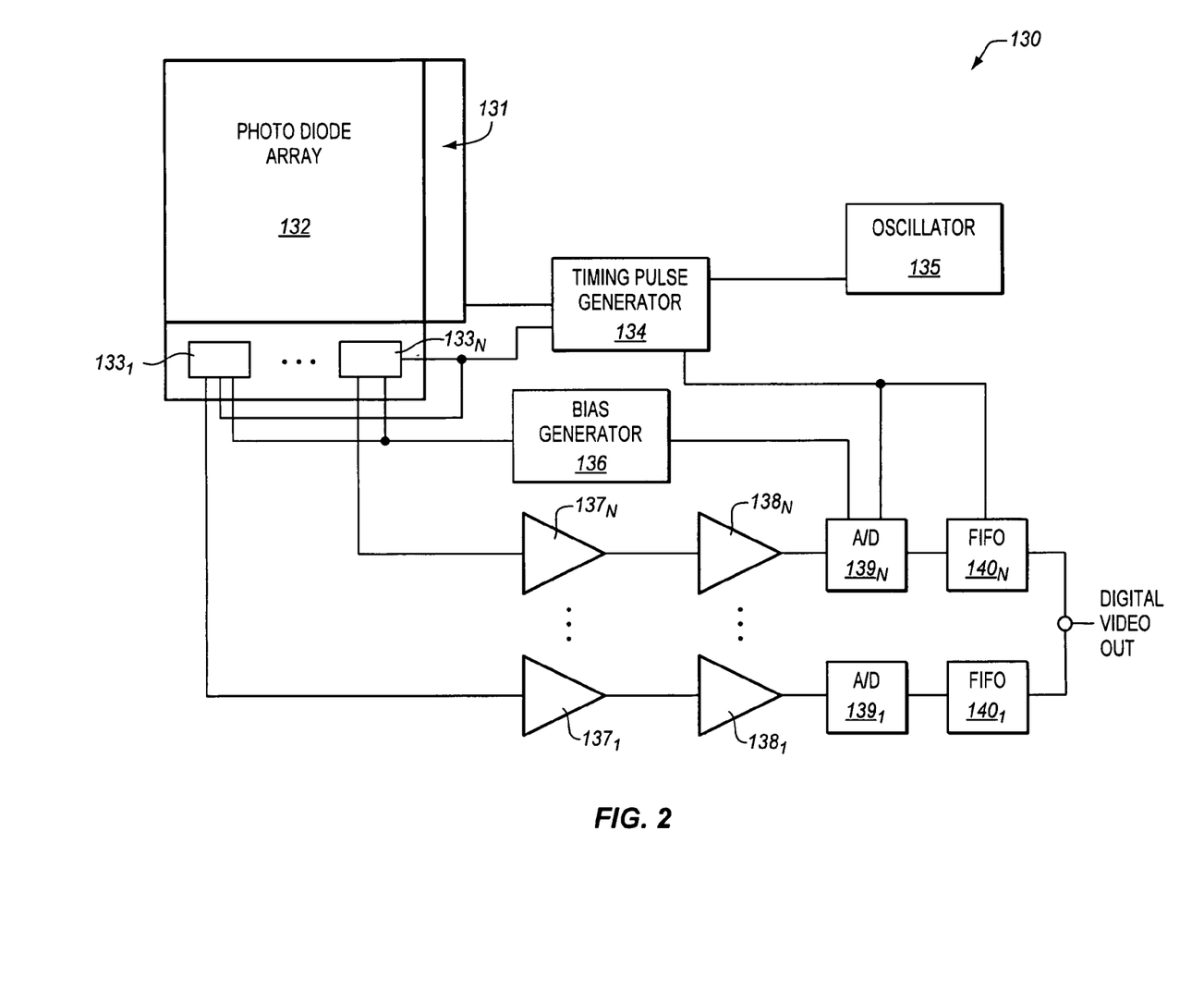
FIG. 2 is a block diagram of an exemplary flat-panel sensor.

The digital video output from the flat panel sensor 130 may be configured in a variety of ways. For example, since no two flat panel sensor designs are necessarily alike, the number of bits in the digital video output used to represent the analog information from the photodiode array 132 may vary from device to device. The test bed 10 is able to process the information from a variety of flat panel sensor types by employing a virtually universal connection scheme in the communication link 13. In one embodiment, the communication link 13 includes a zero insertion force connector that is implemented as a printed circuit board configurable with a plurality of connection types. In this regard, the communication link 13 may transfer data from a plurality of flat-panel sensor types.

From there, the computer workstation 11 may manipulate the data according to the flat-panel sensor type. For example, the computer workstation 11 may include software capable of detecting the flat-panel sensor type. In this regard, the software may determine the brand, model, etc. of the x-ray device based on the connection to the flat-panel sensor 14. After determining the x-ray device type (e.g., the flat-panel sensor type), the computer workstation 11 may retrieve software instructions that direct the workstation to process the data from the flat-panel sensor according to the x-ray device type. In this regard, the computer workstation 11 may analyze the data received from the flat-panel sensor 14 to determine whether the flat-panel sensor 14 and/or the x-ray tube 18 are operating as designed, or within some standard, regulation, or guideline.

Based on the data received from the flat-panel sensor 14, if it is determined that the flat-panel sensor 14 and/or the x-ray tube 18 are not operating as desired, then certain components can be replaced or repaired. For example, the photodiode array 132 of the flat-panel sensor is not something that can be easily repaired because the individual photodiodes of the flat-panel sensor are generally constructed through a semiconductor process that forms the entire array. As such, individual pixel detectors (e.g., photo diodes) are semiconductor devices that are not so discretely connected to one another. However, other ancillary components with the flat-panel sensor 14 may be replaceable. For example, the entire photodiode array 132 may be replaced should an intolerable number of inoperable pixels be determined. In this regard, the control circuitry, such as the amplifiers 133, 137, 138, the timing pulse generator 134, the bias generator 136, the A/D converters 139, etc. could remain and coupled to the replacement photodiode array. More likely, it is these circuits, (e.g., the amplifiers 133, 137, 138, the oscillator 135, the FIFOs 140, etc.) that are likely to fail over some period of time. By analyzing the data from the flat-panel sensor 14, the computer workstation 11 may indicate which part is inoperable such that the circuit can be replaced. Generally such components are configured on printed circuit boards as electronic devices (e.g., ASICs, computer chips, etc.) and can be replaced with relatively careful soldering techniques. Additionally, these components are often purchased in bulk at prices that make the repair of the flat-panel sensor 14 much more cost effective than replacing the entire sensor.

Referring back to FIG. 1, the test bed 10 may also be configured with wheels 16. The wheels 16 may be configured in a variety of ways that serve to make the test bed 10 mobile. In this regard, the test bed 10 would not require a test "station" to identify inoperable and/or marginally operable components. That is, the wheels 16 may provide a repair technician with a certain level of flexibility when repairing the x-ray device.

Figure 3:
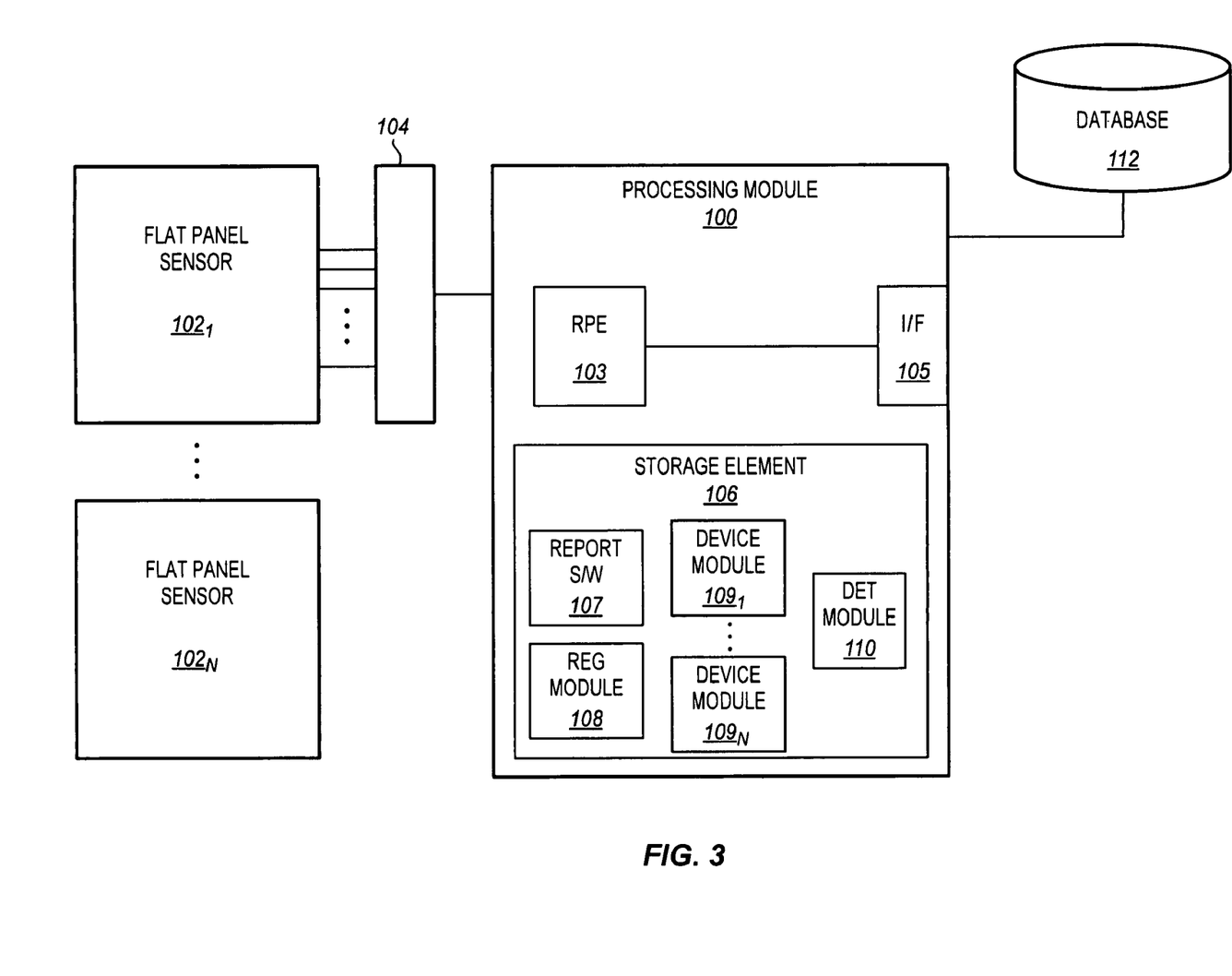
FIG. 3 is a block diagram of an exemplary x-ray test bed processing module.

FIG. 3 is a block diagram of an exemplary x-ray test bed processing module 100. The processing module 100 may be implemented as a general-purpose processor such as that used by the computer workstation 11. Alternatively or additionally, the processing module 100 may be configured as a computer card is operable within the constructs of a computer workstation. In any case, the processing module 100 is configured with a communication interface 104 that communicatively couples the processing module 100 to a variety of different flat-panel sensor types (e.g., the flat-panel sensors $102_{1 \ldots N}$). As described hereinabove, the communication interface 104 may, therefore, be configured in such a way so as to adaptively transfer data from a variety of flat panel sensor types. For example, the communication interface 104 may be a printed circuit board that is used to implement a zero insertion force connection to multiple flat-panel sensor types.

Once a flat-panel sensor $102_1$ is coupled to the communication interface 104, the processing module 100 may retrieve a device detection software module 110 from the storage element 106 for processing by the rules processing engine 103. For example, the device detection software module 110 may include software instructions that direct the rules processing engine 103 to generate control signals that interrogate the connectors of the communication interface 104. Based on the connections between the flat-panel sensor $102_1$ and the communication interface 104, the rules processing engine 103 may determine the type of the flat-panel sensor $102_1$ (i.e., or any other flat-panel sensor 102 coupled thereto).

Once determined, the rules processing engine 103 may retrieve a device specific software module 109 to initiate testing of the flat-panel sensor 102. For example, once the rules processing engine 103 determines the type of flat-panel sensor $102_1$, the rules processing engine 103 may call the device specific software module $109_1$ that contains software instructions specific to the flat-panel sensor $102_1$. In this regard, the software module $109_1$ may direct the rules processing engine 103 to, among other things, format data from the flat-panel sensor 102 according to a manner in which the data would be typically processed. For example, if the flat-panel sensor $102_1$ generates 13 bit video out data, the rules processing engine 103 may be directed by the software module $109_1$ to format the data from the flat-panel sensor accordingly. Similarly, if the flat-panel sensor $102_N$ outputs video data in a 16-bit format, the software module $109_N$ may direct the rules processing engine 103 to format the data accordingly.

Additionally, the device specific software modules 109 may direct the rules processing engine 103 to display the digital video data according to the flat-panel sensor 102 type. In one embodiment, the software modules 109 may include ImageJ software instructions (i.e., Java image processing software) that format the data for display via a display module, such as the computer monitor 12 of FIG. 1.

In this regard, the software instructions from the device specific software module 109 may direct the rules processing engine 103 to transfer formatted video data to the interface 105 for display to a technician. For example, the interface 105 may be communicatively coupled to a display module, such as a computer monitor (e.g., an LCD TV, CRT monitor, or the like), such that the technician may observe the operational characteristics of an x-ray tube and/or the flat-panel sensor 102. Based on those observed operational characteristics, the technician may determine components that are either inoperable or partially inoperable. For example, the technician may observe the frequency response of an x-ray tube by testing the x-ray tube on a material with known x-ray characteristics (e.g., placing the material between the x-ray tube and the flat-panel sensor). Additionally or alternatively, the technician may observe certain features in the displayed data that indicate one or more inoperable components with the flat-panel sensor. For example, intermittent data may indicate a faulty oscillator being used to clock out charges from the photo diode array. In any case, the displayed data may indicate, to the technician, components within the flat-panel sensor 102 and/or an x-ray tube that require repair.

In one embodiment, a device specific software module 109 directs the rules processing engine 103 to access a database 112 to retrieve additional information pertaining to the flat-panel sensor 102 and/or the x-ray tube under test. For example, the database 112 may store device specific information according to x-ray device type. Such information may include, among other things, observed component failure data that may also be used to indicate possible failures within the flat-panel sensor 102 and/or the x-ray tube.

Additionally, the storage element 106 may include a report software module 107 and a regulatory information software module 108. The regulatory information module 108 may direct the rules processing engine 103 to determine whether a flat-panel sensor 102 is operating within a particular standard. For example, individual photodiodes within a flat-panel sensor 102 may fail. If the number of individual photodiodes that fail is beyond some requisite number of operable photodiodes within a regulatory scheme (e.g., a food and drug administration regulation), the regulatory information software module 108 may determine such and require that at least the photo diode array of the flat-panel sensor 102 be replaced. Generally, the flat-panel sensor 102 is often equipped with software that compensates for the failed pixels within the entire photo diode array. Still, if the number of photodiodes that fail is beyond some ability of the software to compensate for the failed pixels, may determine such and require that at least the photo diode array of the flat-panel sensor 102 be replaced. Moreover, the regulatory information software module 108 may determine the number of operable pixels remaining and a failure rate to determine a life expectancy of the flat panel sensor 102. For example, if a number of pixels has failed but not beyond a regulatory limit, the regulatory information software module 108 may determine a rate at which the pixels are failing to determine when the flat panel sensor 102 is likely to breach the regulatory limit.

The report software module 107 may direct the rules processing engine 103 to generate a report that includes information pertaining to certain determinations made by the processing module 100. For example, the report software module 107 may direct the rules processing engine 103 to generate reports pertaining to a number of operable pixels within the flat-panel sensor 102 (e.g., a percentage of operable pixels), performance within a regulatory guideline, and expected lifetime for the flat-panel sensor 102, etc. Such information, once generated, may be transferred to the communication interface 105 for display via a display module or other data display means (e.g., printer, electronic file creation, etc.).

Figure 4:
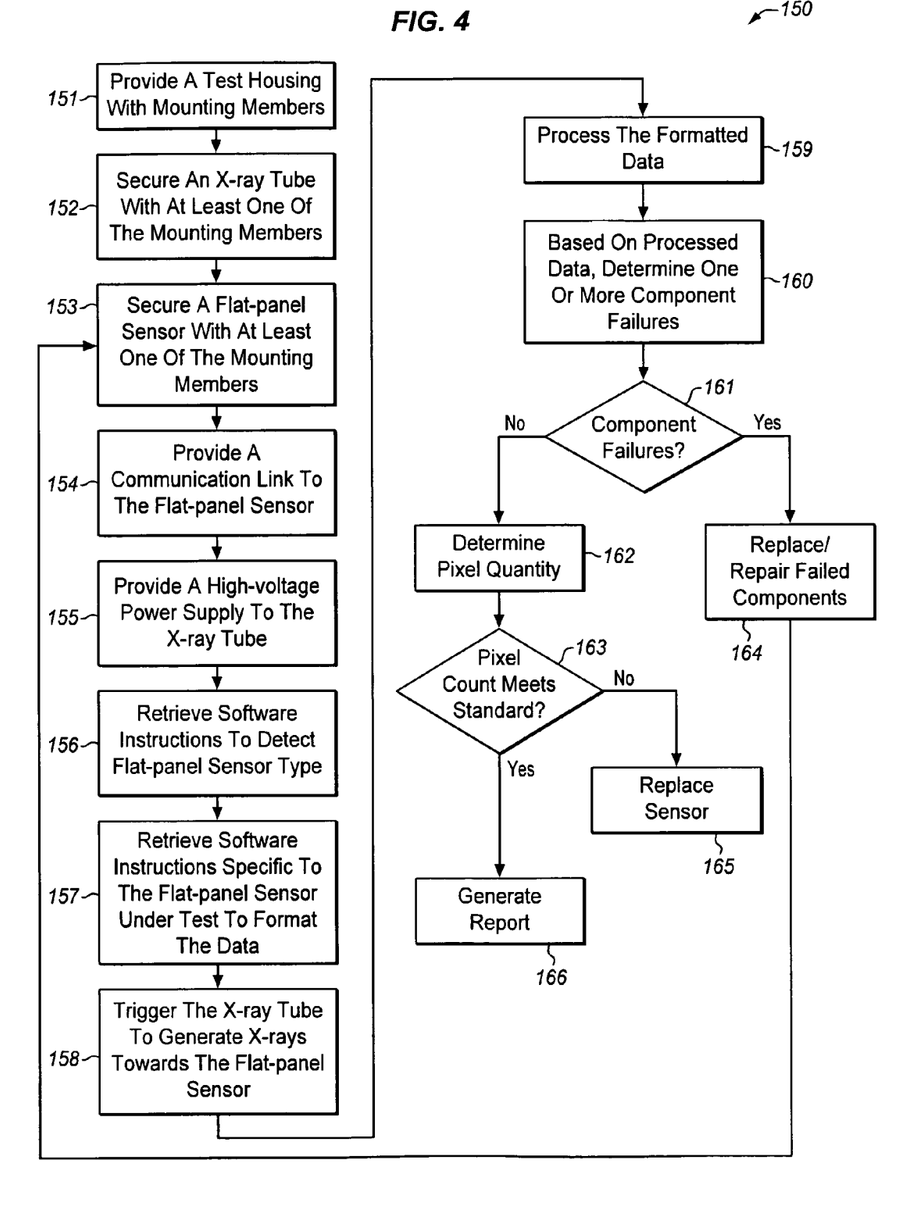
FIG. 4 is a flowchart of a process for testing an x-ray device.

FIG. 4 is a flowchart of a process 150 for testing an x-ray device. In this embodiment, a test housing that includes mounting members is provided, in the process element 151. For example, an x-ray tube may be secured with one of the mounting members (process element 152) and a flat-panel sensor of the x-ray device may be secured within another mounting member (process element 153) such that the x-ray tube radiates in the direction of the flat-panel sensor. This "test bed" also provides a communication link to the flat-panel sensor under test, in the process element 154, for transferring data from the flat-panel sensor to a processing module, such as a computer workstation, to determine the operational characteristics of the x-ray device. Since the test bed may be configured for testing a plurality of different flat-panel sensor types, the data from the flat-panel sensors may come in a variety of different formats. In this regard, the communication link may be configured for coupling to a plurality of flat-panel sensor types. In one embodiment, the communication link may include a zero insertion force connector that is configured as a printed circuit board with connector layouts that provide connections to a plurality of plurality of flat-panel sensor types.

The test bed also provides a high voltage power supply to the x-ray tube, in the process element 155. The high-voltage power supply may be variable so as to provide a changeable voltage to a plurality of different x-ray tube types. For example, x-ray devices from different manufacturers may vary in terms of x-ray tube types and their requisite voltages for generating x-rays. Thus, a variable high voltage power supply may allow for the testing of a plurality of different x-ray tube types.

With the communication link established between the flat-panel sensor and the processing module, software instructions may be retrieved or used to detect the flat-panel sensor type. For example, the software instructions may direct the processing module to generate control signals that are used to interrogate connections of the communication link, in the process element 156. Based on the interrogated connections, the processing module may determine the type of flat-panel sensor being tested and retrieve software instructions that are specific to that flat-panel sensor, in the process element 157.

Once the flat-panel sensor and the x-ray tube are secured with the test housing, the x-ray tube may be triggered to generate x-rays towards the flat-panel sensor, in the process element 158. The device specific software instructions, of the process element 157, may format the data according to the flat-panel sensor under test. For example, flat-panel sensors of x-ray devices operate in a variety of data formats that may depend on the number of individual devices (e.g., photodetectors) configured with the devices. A timing device (e.g., an oscillator) may clock out electronic data from the individual devices in a particular format once the device converts received x-ray radiation (e.g., photons). Once received, the software instructions may format the data for processing in a manner consistent with the original electronic data format of the flat-panel sensor.

Thereafter, the processing module may process the formatted data for analysis, in the processing element 159. The processed data may be displayed via a display module such as a computer monitor for analysis by a technician. For example, the displayed data may indicate certain correctable failures, such as the improper timing of data being clocked out from the flat-panel sensor. The technician may analyze the displayed data to determine component failures with the flat-panel sensor and/or the x-ray tube, in the process element 160. If there are component failures (the process element 161), those components may be replaced or repaired, in the process element 164. Generally, such failures occur in ancillary circuitry and can be replaced. For example, oscillator circuitry, amplifier circuitry, and other circuitry are often configured as ASICs and mounted on a printed circuit board. Should a particular ASIC fail, that ASIC may be removed from the printed circuit board and replaced with a similar component. Once repaired, the process 150 may return to the process element 153 to reinitiate testing of the x-ray device components.

If there are no component failures (the process element 161), the test bed may determine a pixel quantity, in the process element 162. For example, as the processing module processes the data from the flat-panel sensor, the processing module may determine a percentage of the flat-panel sensor having operable pixels. The software structures may also include certain standards or regulations that the x-ray device under test must meet. In this regard, the process 150 may determine whether the pixel count meets a requisite standard in the process element 163 by comparing the operable pixel quantity in the process element 162 to the standard. Generally, inoperable pixels cannot be simply replaced because they are often a part of a larger semiconductor manufacturing process. Accordingly, if the flat-panel sensor does not meet the requisite standard, the flat-panel sensor may be replaced, in the process element 165. However, if the number of operable pixels meets or exceeds the standard, a report may be generated, in the process element 166. In this regard, the report may be used by a medical industry segment (e.g., a hospital, a doctor's office, etc.) as a basis for reliance. That is, the medical industry segment may use the report as assurance that it is complying with certain standards and/or regulations. Alternatively or additionally, the processing module may determine a rate at which the pixels are failing source to provide a life expectancy for the flat-panel sensor.

Figure 5:
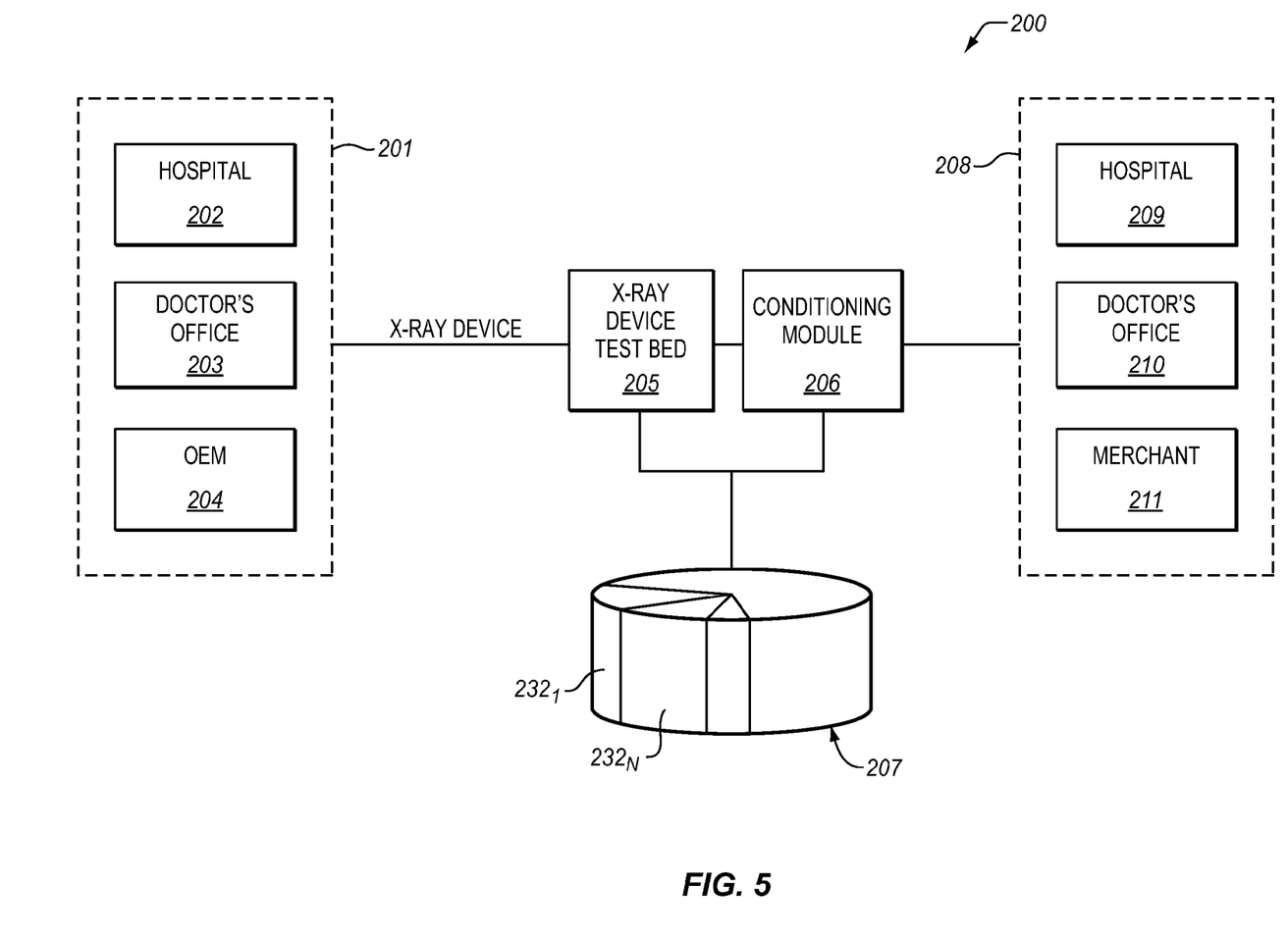
FIG. 5 is a system level block diagram for reintroducing an x-ray device into a medical industry segment.

FIG. 5 is a system level block diagram 200 for reintroducing an x-ray device into a medical industry segment. In this embodiment, an x-ray device is acquired from a medical industry segment 201. The medical industry segment 201 may include a variety of different organizations, such as hospitals 202, doctor's offices 203, and even original equipment manufacturers 204. These organizations typically experience breakdowns in their x-ray devices. These x-ray devices are often costly to replace. However, repair these devices has generally been limited to component level replacement, such as replacing an entire flat-panel sensor even though the flat-panel sensor may be repaired by replacing certain inoperable components configured with the flat-panel sensor. Even an original equipment manufacturer 204 will find it easier to replace an entire flat-panel sensor than to repair the sensor.

In this regard, the x-ray device may be acquired and configured with the x-ray device test bed 205. For example, a repair facility may receive the x-ray device from the medical industry segment 201. This transfer of the x-ray device from the medical industry segment 201 to the repair facility may result in a transfer of the title of the x-ray device to the repair facility. From there, the repair facility may configure the x-ray device with the test bed 205 by securing the flat-panel sensor of the x-ray device with the test bed and coupling a communication link thereto. The repair facility 205 may also secure the x-ray tube of the x-ray device with the test bed to test the operability of the x-ray tube. However, since flat-panel sensors may generally operate with a variety of x-ray tube types, the x-ray test bed may be configured with a standard x-ray tube that is used to test a plurality of flat-panel sensors.

In any case, the test bed 205 may be linked with a conditioning module 206 to return the x-ray device to an operable status. For example, the x-ray device test bed 205 may extract data from the x-ray device under test that indicates the inoperability of one or more components of the x-ray device. Once those components have been identified, a conditioning module 206 may be used to replace and/or repair those components.

In one embodiment, the x-ray device test bed 205 and/or the conditioning module 206 are linked with a database 207 that is used to compile data pertaining to x-ray devices. For example, when one x-ray device has been tested, data pertaining to inoperable features and various failure rates of components of the x-ray device may be compiled and stored with the database 207. The conditioning module 206 and/or the x-ray device test bed 205 may retrieve such information when encountering a similar x-ray device such that the inoperable components can be more readily identified and repaired.

Once repaired, the x-ray device may be transferred to a medical industry segment 208. For example, the x-ray device may be transferred to a hospital 209, a doctor's office 210, a merchant 211, etc. The components of the medical industry segment 208 to which the x-ray device may be transferred may be the same or different from the components of the medical industry segment 201. For example, since title of the x-ray device may have been transferred when acquired, the title of the x-ray device may be transferred to a different medical industry segment. However, the invention is not intended to be so limited as the x-ray device may be acquired in bailment.

Figure 6:
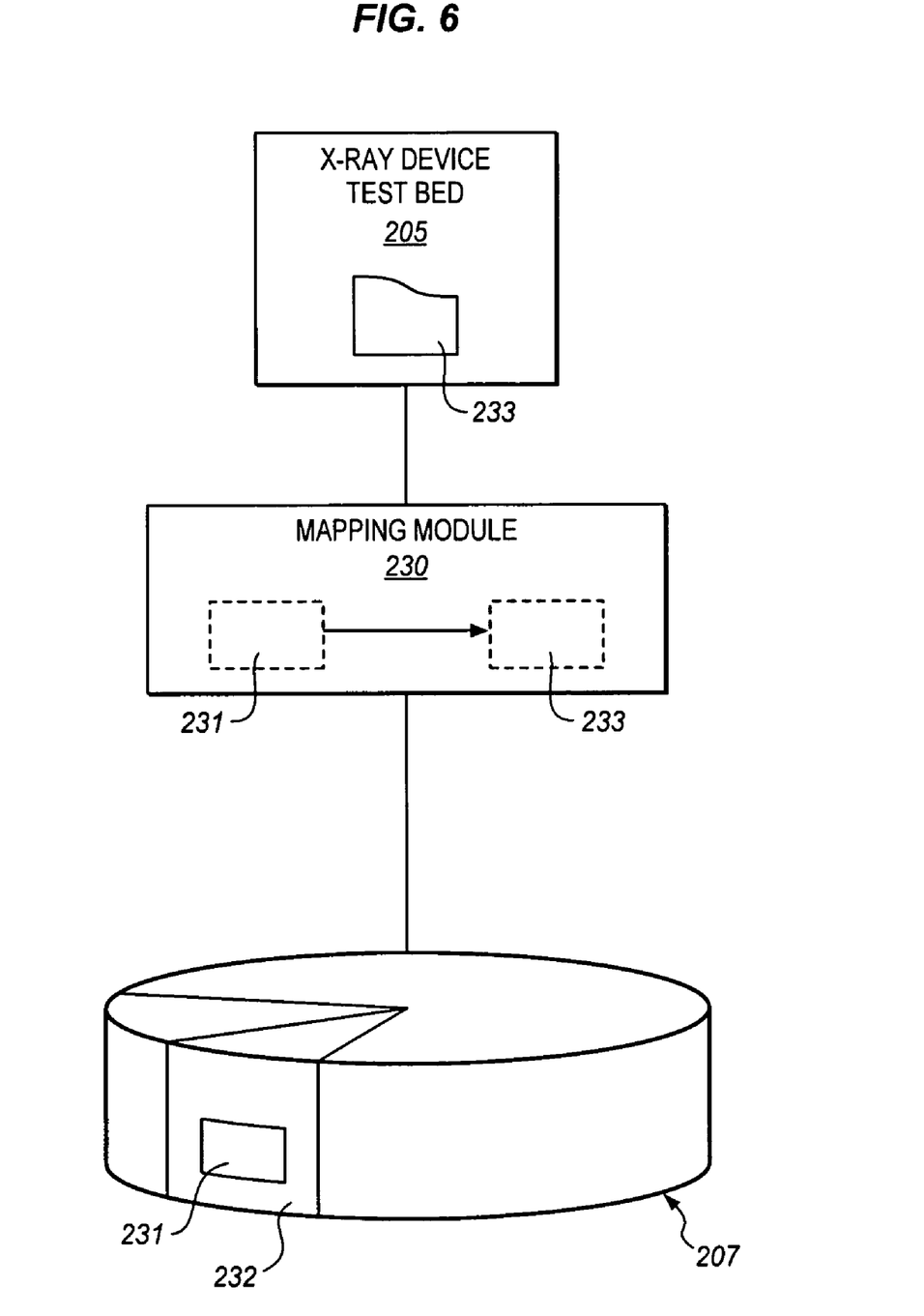
FIG. 6 is another system level block diagram for reintroducing an x-ray device into a medical industry segment that includes a mapping module.

FIG. 6 is another system level block diagram for reintroducing an x-ray device into a medical industry segment that includes a mapping module 230. The mapping module 230, of this embodiment, maybe used to retrieve data from the database 207 per mapping to information pertaining to an x-ray device under test. For example, the x-ray device test bed 205 may acquire certain information 233 pertaining to the x-ray device under test. This information 203 may include schematic information, electronic component information, flat-panel sensor type information, and the like. Such information may have been previously acquired during the testing of a similar x-ray device. The previously acquired information 231 may be stored in a database 207 and categorized within the database 207 by device type. For example, the database 207 may include sectors $232_{1 \ldots N}$ that are each reserved for storing information pertaining to a particular x-ray device. The mapping module 230 may retrieve this previously acquired information 231 from the database 207 for comparison to the newly acquired information 233. In this regard, the mapping module 230 may identify certain features of the newly acquired information 233 (e.g., flat-panel sensor type, data formatting, circuit diagrams, etc.) that are relevant to the previously acquired information 231. The mapping module 230 may then use the information 231 to supplement the information 233. That is, the mapping module 230 may identify portions of the information 233 that have yet to be fully resolved via the x-ray device test bed 205 but may be resolved by means of the information 231.

In one embodiment, the mapping module 230 is a software module that is configured with the storage element 106 of FIG. 3. In this regard, the rules processing engine 103 may retrieve the mapping module 230 to direct the processing module 100 to retrieve the information 231 (e.g., a copy thereof) from the database 207 for comparison of the newly acquired data from the x-ray device test bed 205.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected. Additionally, the variable "N" used herein is merely intended to denote an integer greater than 1. It is not intended to necessarily equate one set of devices to another. For example, the number of A/D converters in FIG. 2 denoted by the variable "N" may not equate to the number of flat-panel sensors denoted by the variable "N" FIG. 3. However, the number "N" of flat-panel sensors 102 in FIG. 3 may equal the number "N" of device specific software modules 109 in FIG. 3, although not required.

What is claimed is:

1. A test bed for testing different x-ray devices that include imaging modules and x-ray tubes, including:

a housing that includes a first support member and a second support member, wherein the first support member is configured for retaining one of the x-ray tubes and wherein the second support member is configured for retaining one of the x-ray imaging modules;

a high-voltage power supply configured for selectively providing a plurality of voltage levels and for being adapted to provide at least one of the voltage levels to the x-ray tube; and a processor communicatively coupled to the x-ray imaging module to retrieve electronic data from the x-ray imaging module wherein the processor processes the electronic data to determine at least one inoperable component of the x-ray imaging module; and a storage element that stores a software module, wherein the software module directs the processor to determine a failure rate for the pixels of the x-ray imaging module.

2. The test bed of claim 1, wherein the x-ray imaging modules are manufactured by different manufacturers.

3. The test bed of claim 1, wherein the storage element also stores a software module that directs the processor to generate a report that includes information associated with at least one inoperable pixel of the x-ray imaging module.

4. The test bed of claim 3, wherein the storage element also stores a software module that controls a rules processing engine, wherein the rules processing engine is configured for receiving the information associated with the at least one inoperable pixel of the imaging module to determine a requisite compliance.

5. The test bed of claim 4, wherein the requisite compliance includes a standard, a government regulation, or both.

6. The test bed of claim 1, further including a display interface configured for displaying an image produced by operable pixels of the x-ray imaging module.

7. The test bed of claim 6, wherein the storage element also stores a software module that directs the processor to display a location of at least one inoperable pixel with the display interface.

8. The test bed of claim 1, wherein the storage element also stores a software module that directs the processor to locate the least one inoperable pixel of the imaging module.

9. The test bed of claim 1, wherein the storage element also stores a software module that directs the processor to determine a percentage of operable pixels within the imaging module.

10. A system for analyzing flat panel sensors of x-ray devices to determine operational characteristics of the flat panel sensors, including
    a radiant energy source;
    a high voltage source coupled to the radiant energy source to stimulate emission of radiant energy from the radiant energy source;
    a communication interface configured for adaptively coupling to a plurality of flat panel sensors;
    a processor communicatively coupled to the communication interface to determine a type of flat panel sensor coupled to the communication interface and to process data from the flat panel sensor for use in determining one or more inoperable components of the flat panel sensor.

11. A method of reconfiguring a plurality of x-ray device types, including:
    identifying a first x-ray device of a medical industry segment, wherein the first x-ray device is at least partially inoperable;
    acquiring the first x-ray device from the medical industry segment;
    providing a test bed that adapts to a configuration of the first x-ray device;
    operating the test bed to determine at least one inoperable component of the first x-ray device; and
    replacing or repairing me the at least one inoperable component to return the first x-ray device to an operable status.

12. The method of claim 11, wherein operating the test bed includes accessing a database that stores information associated with a second x-ray device to determine the least one inoperable component of the first x-ray device, wherein the first x-ray device and the second x-ray device include a same type.

13. The method of claim 11, further including storing information, in a database, of at least a portion of the first x-ray device in response to operating the test bed.

14. The method of claim 13, further including:
    identifying a second x-ray device of a medical industry segment, wherein the second x-ray device is at least partially inoperable;
    acquiring the second x-ray device from the medical industry segment;
    providing a test bed that adapts to a configuration of the second x-ray device;
    operating the test bed to determine at least one inoperable component of the second x-ray device; and
    replacing or repairing the at least one inoperable component to return the second x-ray device to an operable status.

15. The method of claim 14, further including storing information, in the database, of at least a portion of the second x-ray device in response to operating the test bed for the second x-ray device.

16. The method of claim 15, further including mapping the information of the second x-ray device to the information of the first x-ray device.

17. The method of claim 15, wherein storing the information of the first and second x-ray devices includes storing the information according to manufacturer, wherein the first and second x-ray devices are different.

18. The method of claim 15, wherein the storing the information of the first and second x-ray devices includes storing the information according to type, wherein the first and second x-ray devices are different.

19. A method of determining an operational characteristic of a flat-panel sensor of an x-ray device, including:
    providing a test bed that includes a communication interface configured for coupling to a plurality flat-panel sensors;
    generating a plurality of control signals to interrogate connections between a first flat-panel sensor and the communication interface;
    determining, based on the interrogated connections, a type of the first flat-panel sensor;
    propagating energy to the first flat-panel sensor;
    extracting data from the first flat-panel sensor in response to propagating energy; and
    processing the extracted data to determine one or more inoperable components configured with the first flat-panel sensor.

20. The method of claim 19, further including:
    coupling a second flat-panel sensor to the communication interface;
    generating a plurality of control signals to interrogate connections between the second flat-panel sensor and the communication interface;
    determining, based on the interrogate connections, a type of the second flat-panel sensor;
    propagating energy to the second flat-panel sensor;
    extracting data from the second flat-panel sensor in response to propagating energy; and
    processing the extracted data to determine one or more inoperable components configured with the second flat-panel sensor.

21. The method of claim 20, further including accessing a database to retrieve information about the first flat-panel sensor for comparison to information about the second flat-panel sensor.

22. The method of claim 21, using the comparison of the information about the first flat-panel sensor to the information about the second flat-panel sensor to determine the one or more inoperable components configured with the second flat-panel sensor.

23. The method of claim 19, further including determining a percentage of operable pixels with the first flat-panel sensor.

24. The method of claim 23, determining a failure rate of pixels with the first flat-panel sensor.

* * * * *